United States Patent

Aichinger et al.

[11] Patent Number: 5,844,964
[45] Date of Patent: Dec. 1, 1998

[54] DIAGNOSTIC INSTALLATION HAVING A DIGITAL IMAGING SYSTEM WITH COMPUTERIZED EVALUATION OF AN IMAGE OF PHANTOM

[75] Inventors: Horst Aichinger, Fuerth; Sigrid Joite-Barfuss, Erlangen; Helmuth Schramm, Neunkirchen; Siegfried Wach, Hoechstadt, all of Germany

[73] Assignee: Siemens Aktiengesellschaft, Munich, Germany

[21] Appl. No.: 928,314

[22] Filed: Sep. 12, 1997

Related U.S. Application Data

[63] Continuation-in-part of Ser. No. 735,590, Oct. 23, 1996, abandoned.

[30] Foreign Application Priority Data

Nov. 6, 1995 [DE] Germany .................. 195 41 300.8

[51] Int. Cl.[6] .................................................. G01D 18/00
[52] U.S. Cl. ................................................................ 378/207
[58] Field of Search ............................................. 378/207

[56] References Cited

PUBLICATIONS

"Evaluation of a Low–dose Digital X–ray System with Improved Spatial Resolution," Martinez–Dávalos et al., Nuclear Instruments and Methods in Physics Research, vol. A 348 (1994) pp. 241–244 no month.

"X–ray Examination with an Improved X–ray Television Unit," Matsuda et al., Am. J. of Roentgenology, vol. 89 (1963), pp. 432–438 no month.

*Primary Examiner*—Craig E. Church
*Attorney, Agent, or Firm*—Hill & Simpson

[57] ABSTRACT

An X-ray diagnostic installation includes an X-ray source and a radiation receiver and a digital imaging processing system, the digital imaging processing system including a computer which evaluates an X-ray image of a phantom by identifying visible details in the X-ray image of the phantom. The computer employs these identified visible details to automatically construct a contrast-detail graph of the phantom. The computer thus undertakes an automatic judgment of the imaging quality, without the need for a trained observer.

1 Claim, 2 Drawing Sheets

DIAGNOSTIC INSTALLATION HAVING A DIGITAL IMAGING SYSTEM WITH COMPUTERIZED EVALUATION OF AN IMAGE OF PHANTOM

This is a continuation-in-part of application Ser. No. 08/735,590, filed Oct. 23, 1996 now abandoned.

BACKGROUND OF THE INVENTION

1. Field of the Invention

The present invention is directed to an X-ray diagnostic installation having a digital imaging system, and in particular to an X-ray diagnostic installation wherein a computerized evaluation of an image of a phantom is undertaken in the digital imaging system.

2. Description of the Prior Art

X-ray diagnostic installations are known in which the image information is present in digital form and the X-ray image is optimized using an imaging computer. This is also referred to as image processing in order to indicate that, using the imaging computer, quantitative evaluations of the image content are also possible with regard to various problems concerning image quality. A CCD transducer, for example, can be used as an image sensor in such an installation.

In an X-ray diagnostic installation, it is necessary to be able to judge the imaging quality of the imaging system. For this purpose, it is known to use test bodies, e.g. drilled-hole or cylinder phantoms with different hole diameters or different cylinder diameters and different hole depths or cylinder heights. These phantoms permit the calculation of a contrast-detail graph. In the X-ray image of a correspondingly constructed phantom, the individual objects are respectively recognized or not recognized by an observer, dependent on the amount of contrast and the size of the object. It is thus possible to plot a curve in the image that divides details that are visible, given imaging with a specific system, from the invisible details. It is then possible to produce a graph called a contrast-detail graph. All radiological image generation systems have in common the property that an object with a particular contrast is better visible the larger it is, and that an object of a predetermined size is better visible the greater its contrast. From these facts, a typical curve of a contrast-detail graph results. The specific curve is, however, different for each image generation system, and permits an estimate of its imaging quality characteristic. The calculation of contrast-detail graphs by several observers is very costly and time-consuming.

SUMMARY OF THE INVENTION

An object of the present invention is to provide an X-ray diagnostic installation of the type described above wherein a contrast-detail graph is automatically produced.

The above object is achieved in accordance with the principles of the present invention in an X-ray diagnostic installation having an X-ray source, a radiation receiver which receives X-rays from the X-ray source, attenuated by a patient, and a digital imaging system including an imaging computer, the imaging computer including an algorithm which evaluates the image of a phantom by identifying visible details of the phantom in the X-ray image thereof and constructing a contrast-detail graph therefrom.

In the inventive X-ray installation, the imaging computer is used for the construction of the contrast-detail graph. In principle, the invention is suitable for use in any digital imaging system with its own imaging computer. The invention offers the advantage that the evaluation process can be carried out rapidly and without a trained observer.

DESCRIPTION OF THE PREFERRED EMBODIMENTS

Figure 1:
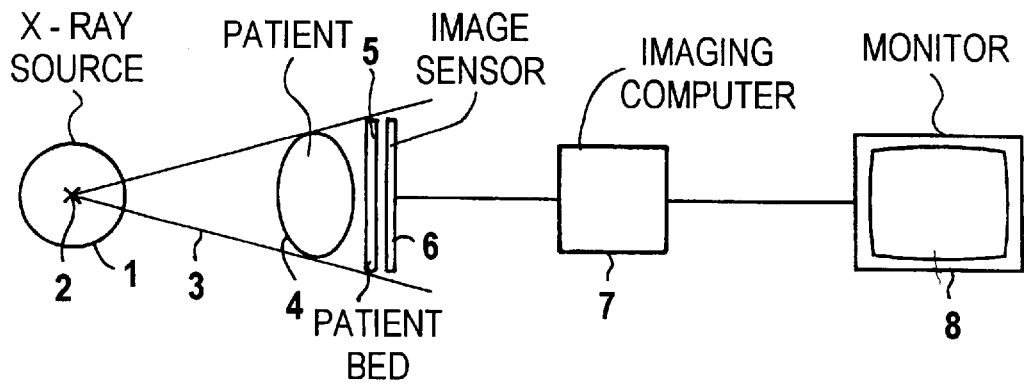
FIG. 1 is a schematic block diagram of an X-ray diagnostic installation according to the invention.

FIG. 1 shows an X-ray source 1 having a focus from which an X-ray beam 3 emanates, which penetrates a patient 4 positioned on a bed 5. X-ray images are generated by an image sensor 6, e.g. by a CCD transducer, whose signals are supplied to an imaging computer 7. The imaging computer 7 calculates the X-ray image, which is reproduced on a monitor 8.

Figure 2:
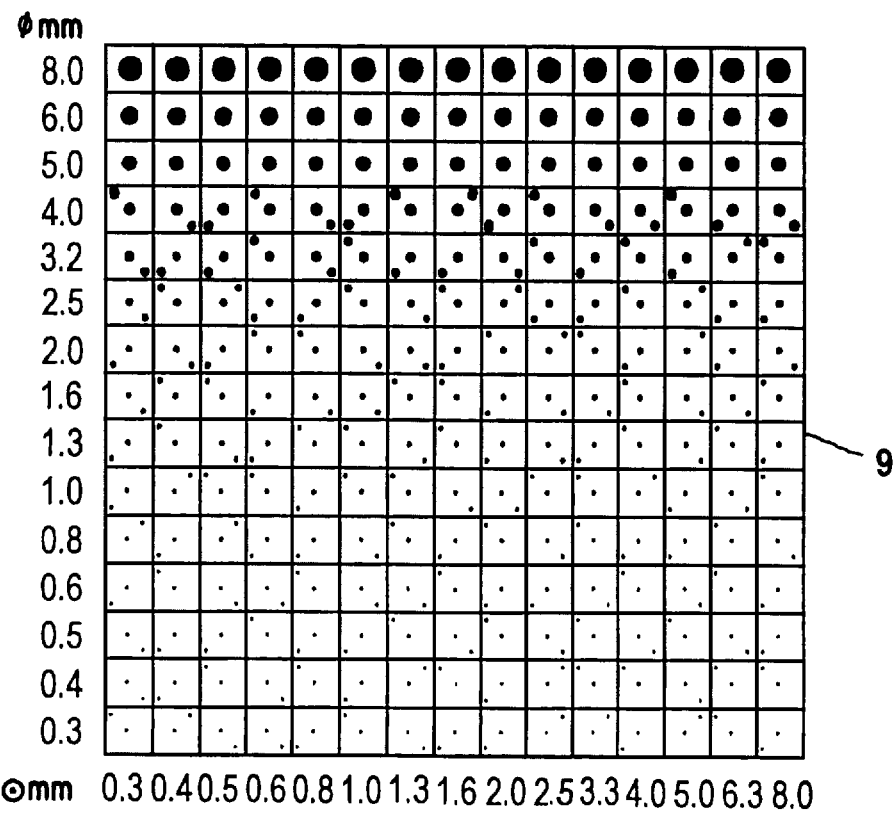
FIG. 2 shows a phantom for judging the imaging quality in the X-ray diagnostic installation according to FIG. 1.

For quality control, i.e. for judgement of the imaging quality, in the exemplary embodiment a plexiglas drilled-hole phantom 9 according to FIG. 2 is used, made of a plexiglas plate with a plurality of drilled holes with various diameters and various hole depths. The drilled-hole phantom 9 is positioned in the X-ray beam 3 in place of the patient 4, for exposure testing or also for constancy testing with the user.

An algorithm integrated in the imaging computer 7 simulates one or several human observers, and evaluates the imaging of the cylinder phantom or the drilled-hole phantom. The imaging computer 7 thus independently looks for the visible details in the X-ray image, and determines at what contrast and at what object size the detail is no longer visible due to the noise of the imaging system. The imaging computer 7 should be used so that it replaces the human observer completely, thereby enabling a more objective observation.

Changes in the image quality due to alterations of the system parameters or a defect in a component of the imaging system can thereby be recognized and removed more rapidly, with evaluations of phantom exposures carried out cyclically. It is also possible to compare different modalities of this system with one another. The evaluation of the exposures with different modalities should then produce significant differences in the contrast-detail graph.

Figure 3:
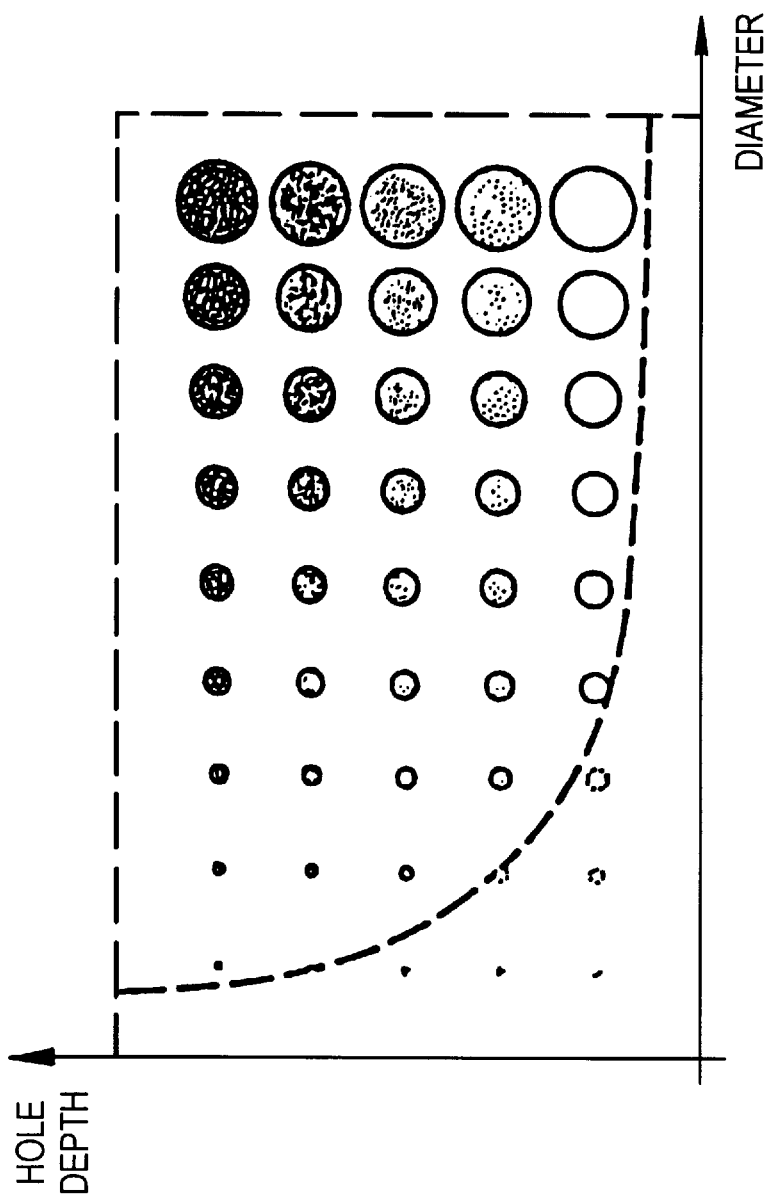
FIG. 3 is a schematic representation of a contrast-detail graph produced by and for the X-ray diagnostic installation of FIG. 1.

As an example, FIG. 3 shows a contrast-detail graph constructed on the basis of the drilled-hole phantom 9, using the imaging computer 7. The diameter is thereby plotted on the abscissa, and the depth of the drilled holes of the drilled-hole phantom 9 is plotted on the ordinate.

The contrast-detail curve does not necessarily have to be observed on the monitor 8. A contrast-detail curve can also be printed at a printer, or prepared as a hard copy using a high-resolution camera.

The evaluation program consists of 3 separate C programs that can be called successively:

1. CDSCORE

\*Input of the observer data
    \*Storing of the values
   1 file with the extension · CDF per observer
  \*Calculation of two image quality characteristics:
     Fractions of good responses:

-continued $FGR = n/N$   $n$: number of correctly recognized fields
$N$: total number of fields
Corrected for guesses:
$CFG = (n + 0.25 * n_0)/Nn$:   number of fields for which no valuation was produced; i.e. misrecognized fields are not taken into account

2. CDMEAN

Formation of mean value over several observers

Calculation of the CD curve by means of determination of the "threshold value" contrast for each diameter First the individual observations are summed and the mean is formed; correctly recognized counts as 100%; not recognized or misrecognized: 25%

A matrix thereby results in the form: As contrast, the absorbed radiation in the gold vapor plating of height H is assumed.

$\mu$=absorption coefficient of gold,
$C=1-\exp(-\mu*H)$ is assumed approximately as a constant
$\mu$=0.193 1/$\mu$m (at 18 keV)

Next the following function is adapted line by line (same diameter, different vapor plating thickness):

$$y = 25 + \frac{75}{1 + \exp(a * (\log C - b))}$$

a, b fit parameters
a=const for all diameters
b determines the threshold contrast:
for log C=b→y=25+75/2=62.5, i.e. $C_s=10^b$ The associated vapor plating thickness H can be back-calculated via $$C_s = 1 - \exp(-\mu * H) \rightarrow \exp(-\mu * H) = 1 - C_s \rightarrow$$
$$-\mu * H = \ln(1 - C_s) \rightarrow H = \ln(1 - C_s)/(-\mu)$$

For further processing with CDFIT, the following values are stored under the filename CDMEAN.LIN:
Diameter d, $C_S*100$, H and a.

3. CDFIT

Adaptation of the points of the CD curve determined by the program CDMEAN to the function $$\log (C_S)=P_1+P_2*\exp\{P_3*\log (d)\}$$

$C_S$=threshold value contrast
d=diameter
$P_1$, $P_2$, $P_3$=fit parameters

The program SDVFIT from the book "Numerical Recipes" by W. H. Press, B. P. Flannery, S. A. Teukolsky and W. T. Vetterling is thereby used.

Storing of the values as a text file or prepared for output for Harvard Graphics Portions of the above are described in further detail in Angerstein, W., Über die Bildgüte in der Radiologie II. Teil: Halbobjektive Bildgütemaβe, Bildunschärfe, Röntgenpraxis 20, 12:278–290, 1967;

Angerstein, W., S. Gursky, H. Hegewald, Strahlenphysik und radiologische Technik in der Medizin, VEB Georg Thieme Verlag Leipzig, 1987;

Bijkerk, R., Lindeijer, J., C/D Fantoom voor Mammographie: Wat zijn de specifikaties?, Projekt QAMAM, Sektie Fysica en Informatica, Academisch Ziekenhuis Nijmegen, 1992; and Burger, G. C. E., Phantom Tests with x-rays, Philips Technical Review, vol. II, no. 10:291–298, 1950.

The following describes phantom exposures with the radiator P49MoW with and without grid voltage.

A check was made to determine whether the application of a grid voltage to the radiator P49MoW has an influence on the image quality. This is a radiator with two anode materials, F1 Mo, F2 W, respectively with 0.3 IEC focal spot, i.e. no microfocus.

The exposures with the Mo focal spot path were made at 25 kV with an additional 2 cm of Plexiglas and with the W focal spot path at 30 kV with an additional 7 cm of Plexiglas. The phantom lay at 2 cm of Plexiglas in order to obtain a constant enlargement factor of m=1.06.

The exposures were evaluated by five different observers; one observer carried out the evaluation twice, so that six individual results were available.

| | Comparison with and without grid voltage | | | | | | | |
|---|---|---|---|---|---|---|---|---|
| | Exposure 2 Anode Mo Ug off kV 25 mAs 48.8 cm Plexi 2 | | Exposure 3 Anode Mo Ug = 40 V on kV 25 mAs 48.6 cm Plexi 2 | | Exposure 7 Anode W Ug = 40 V on kV 30 mAs 640 cm Plexi 7 | | Exposure 8 Anode W Ug off kV 30 mAs 640 cm Plexi 7 | |
| Observer | FGR | CFG | FGR | CFG | FGR | CFG | FGR | CFG |
| 1 | 0.683 | 0.762 | 0.688 | 0.765 | 0.507 | 0.630 | 0.556 | 0.667 |
| 2 | 0.693 | 0.766 | 0.732 | 0.799 | 0.551 | 0.662 | 0.541 | 0.655 |
| 3 | 0.722 | 0.784 | 0.756 | 0.812 | 0.551 | 0.661 | 0.527 | 0.644 |
| 4 | 0.654 | 0.740 | 0.683 | 0.760 | 0.507 | 0.629 | 0.483 | 0.611 |
| 5 | 0.688 | 0.765 | 0.707 | 0.778 | 0.512 | 0.633 | 0.517 | 0.638 |
| 6 | 0.722 | 0.790 | 0.756 | 0.816 | 0.576 | 0.677 | 0.566 | 0.671 |
| Sum | 4.162 | 4.607 | 4.322 | 4.730 | 3.204 | 3.892 | 3.190 | 3.886 |
| < > | 0.694 | 0.768 | 0.720 | 0.788 | 0.534 | 0.649 | 0.532 | 0.648 |
| Standard deviation | 0.0258 | 0.0177 | 0.0325 | 0.0241 | 0.0293 | 0.0206 | 0.0230 | 0.0220 |

For circuit-related reasons, it would be desirable for the grid voltage also to be present at the large focus, since then no switchover would be required. A negative influence of the grid voltage on the image quality checked with the phantom is not to be expected. In exposures using a W radiator, there results practically no difference, while for molybdenum exposures an improvement can be expected.

Although modifications and changes may be suggested by those skilled in the art, it is the intention of the inventors to embody within the patent warranted hereon all changes and modifications as reasonably and properly come within the scope of their contribution to the art.

We claim as our invention:

1. An X-ray diagnostic installation comprising:

an X-ray source which emits X-rays;

a radiation receiver struck by said X-rays from said X-ray source;

a phantom disposed between said X-ray source and said radiation receiver, said radiation receiver generating electrical signals corresponding X-rays from said X-ray source attenuated by said phantom, said electrical signals comprising, in combination, an X-ray image of said phantom; and digital imaging means for processing, in a computer, an X-ray image of an object disposed between said X-ray source and said radiation receiver for producing a video image of said object, said computer of said digital imaging means containing means for automatically evaluating said X-ray image of said phantom by identifying visible details of said phantom in said X-ray image of said phantom and for constructing a contrast-detail graph therefrom, and said computer of said digital imaging means employing said contrast-detail graph in producing said video image of said object.

\* \* \* \* \*